United States Patent [19]

Foley et al.

[11] 4,140,689
[45] Feb. 20, 1979

[54] 3-(JULOLIDINYL)-BENZ[D]ISOTHIAZOLE-1,1-DIOXIDE

[75] Inventors: James W. Foley, Andover; John W. Lee, Jr., Harvard, both of Mass.

[73] Assignee: Polaroid Corporation, Cambridge, Mass.

[21] Appl. No.: 836,023

[22] Filed: Sep. 23, 1977

[51] Int. Cl.² .................. C07D 491/06; C07D 513/06
[52] U.S. Cl. .................................... 546/94; 96/29 D; 96/84 R
[58] Field of Search .............. 260/283 S, 301, 260, 260/288 CF, 283 SA

[56] References Cited

U.S. PATENT DOCUMENTS

| 3,719,480 | 3/1973 | Brantly | 96/1 PC |
| 3,929,797 | 12/1975 | Borror et al. | 260/287 CE |

FOREIGN PATENT DOCUMENTS

| 2105580 | 9/1972 | Fed. Rep. of Germany | 260/301 |
| 39-08832 | 5/1964 | Japan. | |
| 49-10131 | 6/1974 | Japan. | |

OTHER PUBLICATIONS

Fritsch, Chem. Berichte 29 pp. 2990–2301 (1896).
Abramovitch, et al., J. Chem. Soc. Perkin Trans. I (22) pp. 2589–2594 (1974).

Primary Examiner—Paul M. Coughlan, Jr.
Assistant Examiner—Diana G. Rivers
Attorney, Agent, or Firm—Sybil A. Campbell

[57] ABSTRACT

This invention relates to 3-(julolidinyl)-benz[d]-isothiazole-1,1-dioxide useful as an intermediate in the synthesis of certain 3,3-disubstituted-2,3-dihydrobenz[d]-isothiazole-1,1-dioxide dyes which find utility as, for example, photographic optical filter agents and filter agent precursors.

1 Claim, No Drawings

3-(JULOLIDINYL)-BENZ[D]ISOTHIAZOLE-1,1-DIOXIDE

BACKGROUND OF THE INVENTION

1. Field of the Invention

This invention relates to 3-(julolidinyl)-benz[d]-isothiazole-1,1-dioxide.

2. Description of the Prior Art

Though various 3-substituted-benz[d]isothiazole-1,1-dioxides have been disclosed, only a few 3-aryl derivatives are known. P. Fritsch, Ber., p. 2290 (1896) reported that the 3-phenyl derivative was obtained by the reaction of 3-chlorobenz[d]isothiazole-1,1-dioxide (saccharin pseudo-chloride) and benzene under Friedel-Crafts conditions. The 3-(p-dimethylaminophenyl) derivative was prepared similarly. The 3-(p-chlorophenyl) derivative was obtained by the treatment of ammonium 2-(4'-chlorobenzoyl)benzenesulfonate with phosphorus pentachloride as reported by Z. Horii, Jap. Pat. Nos. 10,131/1964 and 8832/1964. R. A. Abramovitch et al, J. Chem. Soc., Perkin Trans. I, 22, p. 2589 (1974) reported that the reaction of alkyl- and aryllithium compounds with 3-oxo-2,3-dihydrobenz[d]isothiazole-1,1-dioxide (saccharin) in tetrahydrofuran at -78° C. gave the corresponding 3-alkyl or 3-aryl derivatives exclusively and prepared the 3-phenyl, 3-(o-tolyl), 3-(p-methoxyphenyl) and 3-(2-pyridyl) derivatives in this manner. The latter authors also reported that the 3-phenyl derivative was prepared by the treatment of saccharin with two equivalents of phenylmagnesium bromide in tetrahydrofuran at ambient temperature.

Copending U.S. Patent Application Ser. No. 836,025 of Alan L. Borror, James W. Foley, Marcis M. Kampe and John W. Lee, Jr. filed concurrently herewith is directed to a method of synthesizing 3,3-disubstituted-2,3-dihydrobenz[d]-isothiazole-1,1-dioxides possessing a carbonyl group in the 2-position. Depending upon the carbonyl group and the 3,3 substituents, the products of the synthesis may be employed as pH-sensitive indicator dyes, antihalo dyes or photographic optical filter agent precursors. As disclosed and claimed therein, the method of preparing these compounds comprises reacting a 3-(phenyl/naphthyl)-benz[d]isothiazole-1,1-dioxide and a 4'-OP-phenyl/4'-OP-naphthyllithium compound to give the corresponding 3-(phenyl/naphthyl)-3-(4'-OP-1'-phenyl/4'-OP-1'-naphthyl)-2,3-dihydrobenz[d]isothiazole-1,1-dioxide wherein P represents a protecting group compatible with organometallic reagents. The compound thus prepared is then reacted with the selected carboxylic acid halide to give the corresponding 2-carbonyl derivative which is then treated with acid to remove the protecting group and yield the dye product. The phenyl or naphthyl group of the 3-(phenyl/naphthyl)-benz[d]-isothiazole-1,1-dioxide employed in the initial step of the synthesis may be unsubstituted, or it may be substituted with, for example, an alkyl, alkoxy and/or other substituents.

The present invention is concerned with a 3-substituted-benz[d]isothiazole-1,1-dioxide useful as an intermediate in the aforementioned synthesis.

SUMMARY OF THE INVENTION

It is, therefore, the primary object of the present invention to provide a novel 3-substituted-benz[d]isothiazole-1,1-dioxide useful as an intermediate in the synthesis of certain 3,3-disubstituted-2,3-dihydrobenz[d]isothiazole-1,1-dioxide dyes.

Other objects of this invention will in part be obvious and will in part appear hereinafter.

The invention accordingly comprises the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

Specifically, the 3-substituted-benz[d]isothiazole-1,1-dioxide of the present invention may be represented by the formula:

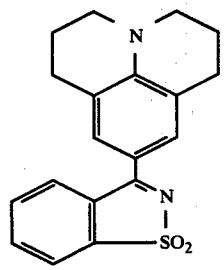

The above compound may be synthesized by reacting julolidine(2,3,6,7-tetrahydro-1H,5H-benzo[ij]quinolizine) with bromine or chlorine with or without a catalyst or with iodinemonochloride to give the corresponding 9-halo derivative which is converted to the corresponding 9-lithium derivative by reaction with lithium metal or n-butyllithium. The lithium derivative is then reacted with the N-lithium salt of saccharin to yield the corresponding 3-(9'-julolidinyl)-benz[d]isothiazole-1,1-dioxide as illustrated in the following reaction sequence.

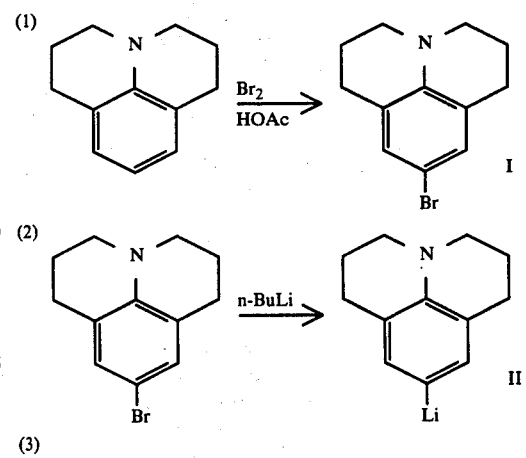

-continued

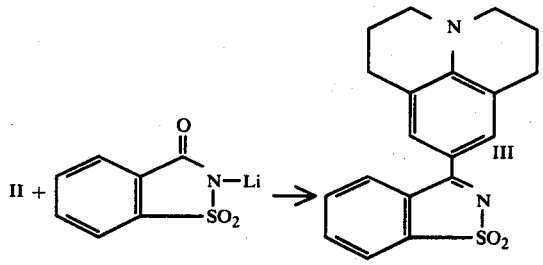

This compound also may be synthesized by reacting the 9-halojulolidine with magnesium metal to give the corresponding Grignard derivative which is then reacted with saccharin pseudo-chloride.

The subject compound was prepared as follows:

(a) Julolidine (100.4 g., 0.579 mol.) was dissolved in 266 ml. of glacial acetic acid. At room temperature, a solution of 29.69 ml. of bromine (0.579 mol.) in 1830 ml. of glacial acetic acid was slowly added to the julolidine solution over a period of about 2½ hours. After the addition was complete, the reaction mixture was stirred for 1 hour. A potassium iodide test for excess bromine indicated no excess present. An additional 1 ml. of bromine was added to the reaction mixture, and the mixture was stirred for ½ hour. The potassium iodide test was repeated and indicated that excess bromine was present. 1000 ml. of ether was added to the reaction mixture which was neutralized by adding 127 ml. (0.637 mol.) of 5N sodium hydroxide. The reaction mixture was further diluted with water and extracted with 2.7 liters of ether. The ether extracts were dried and evaporated to yield a dark oil (105.6 g.). The oil was redissolved in ether and washed with H₂O, the ether was dried over Na₂SO₄ and evaporated to yield a dark oil. The oil was distilled under reduced pressure with a short column to yield three fractions. First fraction, boiling range 123°-125° C. at 11 mm (starting material). Second fraction, boiling range 114°-115° C. at 0.06 mm (mixture). Third fraction, boiling range 120°-122° C. at 0.04 mm (pot temperature 160°-180° C.) contained 21.64 g. of 9-bromojulolidine.

(b) Saccharin (0.08 mol.) was dissolved in about 200 ml. of dry tetrahydrofuran under nitrogen and cooled to −65° C. n-Butyllithium (2.4M) was added dropwise until a persistent peach color occurred. The solution was stirred at −60° C. to −65° C. for 1 hour.

(c) The bromojulolidine prepared in step (a) (20.93 g., 0.08 mol.) was dissolved in 200 ml. of dry tetrahydrofuran under nitrogen and cooled to −60° C. to −70° C. n-Butyllithium was added slowly over one-half hour while maintaining the temperature below −60° C. After the addition was complete, the mixture was stirred for 1½ hours at −60° C. With a double-ended needle, the slurry prepared in step (b) was added to the mixture over 1 hour and stirred for 1 hour at −60° C. The reaction mixture was allowed to come to room temperature in the dark, stirred for 15 hours at room temperature and then hydrolyzed with 100 ml. of saturated ammonium chloride. The mixture was extracted with ether, and the ether extract was evaporated to give 15.40 g. of an orange solid. The solid was dissolved in about 400 ml. of methanol with about 20 drops of conc. HCl and refluxed for 4½ hours. (The orange solid showed a small peak at 466 nm and a larger one at 380 nm and after refluxing, one large peak occurred at 466 nm and none at 380 nm.) The acidic methanol was cooled and filtered, and 6.55 g. of product was collected as a dark red solid. The remaining mother liquor (methanol) was evaporated to yield 9.04 g. of a dark oil. The oil was run through a silica column with chloroform and an additional 1.34 g. of product was collected to yield a total of 7.89 g. of the title compound.

The subject compound also was prepared using the hydrobromide salt of 9-bromojulolidine as follows:

(a) 134 g. (0.758 mol.) of 98% julolidine was dissolved in 500 ml. of glacial acetic acid. To this solution was added a solution of 121 g. (0.758 mol.) of bromine in 2400 ml. of glacial acetic acid. After the addition, the reaction mixture was stirred for 15 minutes and then tested for excess bromine using KI paper. More bromine was added until an excess was detected. The reaction mixture was then stirred for 1 hour at room temperature. The pink solid which formed was collected and washed several times with ether and dried in a vacuum oven overnight to give 245 g. of the hydrobromide salt of 9-bromojulolidine. Yield 92% by weight.

(b) 75 g. (0.22 mol.) of 9-bromojulolidine hydrobromide prepared in step (a) was suspended in 1200 ml. of ether. To the suspension was added 650 ml. of 1N sodium hydroxide and the mixture stirred for 5-10 minutes. The two layers were separated and the aqueous layer was extracted with 1000 ml. of ether. The organic layers were combined, dried over anhydrous calcium sulfate and the ether evaporated to yield 51.97 g. (0.206 mol.) of 9-bromojulolidine as a dark oil.

(c) The 9-bromojulolidine was dissolved in 400 ml. of dry tetrahydrofuran under nitrogen at −65° C. 85.8 ml. of n-butyllithium (2.4M in hexane) was added dropwise giving a tan slurry.

(d) 37.75 g. (0.206 mol.) of saccharin was dissolved in 400 ml. of dry tetrahydrofuran under nitrogen at −65° C. 85.8 ml. (0.206 mol.) of n-butyllithium (2.4M in hexane) was added dropwise until a permanent orange colored endpoint was reached. The mixture was stirred for 1 hour at −65° C., and then used directly in step (e).

(e) The mixture of step (d) was added to the tan slurry of step (c) at −60° C. to −50° C. through a double ended needle. After the addition was completed, the reaction mixture was stirred for 1 hour at −60° C., and gradually warmed to room temperature. The reaction mixture was then poured into 800 ml. of water and the pH adjusted to 5-6 with conc. HCl. The orange precipitate which formed was collected to give 13.9 g. of the title compound. The filtrate was extracted with ether, dried and evaporated to give 46 g. of a dark oil. The oil was washed with hot hexane and then dissolved in hot ethanol (500 ml.) and 75 drops of conc. HCl was added. The ethanol was cooled and 7.53 g. of orange crystals were collected to give the title compound in a total yield of 21.47 g.

As mentioned above, the compounds of the present invention are useful as intermediates in the synthesis of certain 3,3-disubstituted-2,3-dihydrobenz[d]isothiazole 1,1-dioxides possessing a carbonyl group in the 2-position. Such compounds possessing a 4'-hydroxyphenyl moiety as one of the 3,3 substituents and a phenyl/naphthyl or substituted phenyl/substituted naphthyl moiety as the other of the 3,3 substituents form the subject matter of copending U.S. Patent Application Serial No. 836,021 of Stanley M. Bloom, Alan L. Borror and James W. Foley filed concurrently herewith and of copending U.S. Patent Application Ser. Nos. 835,998; 836,005; and 836,009 of Stanley M. Bloom, Alan L.

Borror and James W. Foley also filed concurrently herewith. As discussed in the aforementioned applications, compounds may be selected for use as classical pH-sensitive indicator dyes or as photographic optical filter agents and filter agent precursors depending upon the 2-substituent of the benz[d]-isothiazole ring. The photographic use of those compounds which may be employed as photographic optical filter agents and filter agent precursors forms the subject matter of copending U.S. Pat. application Ser. No. 836,006 of Stanley M. Bloom, Alan L. Borror and James W. Foley filed concurrently herewith.

Since certain changes may be made in the above processes and products without departing from the scope of the invention herein involved, it is intended that all matter contained in the above description shall be interpreted as illustrative and not in a limiting sense.

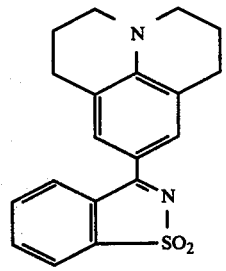

What is claimed is:
1. The compound